US006864795B2

(12) United States Patent
Smith et al.

(10) Patent No.: US 6,864,795 B2
(45) Date of Patent: Mar. 8, 2005

(54) APPARATUS FOR LIGHTING A PATIENT MONITOR FRONT PANEL

(75) Inventors: Toby E. Smith, Broken Arrow, OK (US); Craig L. Cooper, Inola, OK (US); Trevor L. Taylor, Tulsa, OK (US)

(73) Assignee: Bed-Check Corporation, Tulsa, OK (US)

( * ) Notice: Subject to any disclaimer, the term of this patent is extended or adjusted under 35 U.S.C. 154(b) by 337 days.

(21) Appl. No.: 10/125,059

(22) Filed: Apr. 18, 2002

(65) Prior Publication Data

US 2003/0197614 A1 Oct. 23, 2003

(51) Int. Cl.[7] .............................................. G08B 23/00
(52) U.S. Cl. .............................. 340/573.1; 340/573.4; 340/286.07; 340/568.1; 340/686.6; 340/691.1; 340/825.36; 340/825.49
(58) Field of Search ........................ 340/573.1, 573.4, 340/286.01, 286.06, 286.07, 500, 501, 568.1, 573.7, 686.1, 686.6, 825.36, 825.49, 691.1

(56) References Cited

U.S. PATENT DOCUMENTS

| 2,640,144 | A | | 5/1953 | Levy |
|---|---|---|---|---|
| 3,748,769 | A | | 7/1973 | Nolles |
| 4,060,293 | A | | 11/1977 | Waiters |
| 4,354,330 | A | | 10/1982 | Schwartz |
| 4,484,043 | A | | 11/1984 | Musick et al. |
| 4,504,263 | A | * | 3/1985 | Steuer et al. ................. 604/65 |
| 4,565,910 | A | | 1/1986 | Musick et al. |
| 4,577,185 | A | | 3/1986 | Andersen |
| 5,055,977 | A | | 10/1991 | Acquanetta |
| D361,462 | S | | 8/1995 | Newham |
| 5,554,835 | A | | 9/1996 | Newham |
| 5,600,108 | A | | 2/1997 | Newham |
| 5,600,305 | A | | 2/1997 | Stafford et al. |

(List continued on next page.)

FOREIGN PATENT DOCUMENTS

EP 0739069 A1 10/1996

OTHER PUBLICATIONS

Patent Abstracts of Japan, vol. 2000, No. 21 Aug. 3, 2001 & JP 2001 093324 A (Toshiba Lighting & Technology Corp), Apr. 6, 2001.

*Primary Examiner*—Jeffery Hofsass
*Assistant Examiner*—Daniel Previl
(74) *Attorney, Agent, or Firm*—Fellers, Snider, Blankenship, Bailey & Tippens, P.C.; Terry L. Watt

(57) ABSTRACT

There is provided herein an electronic patient monitor that includes indirect lighting of its control panel. Preferably, a splash guard is affixed to the monitor in a position proximate to one or more light sources, none of which directly illuminate the control panel. Light from the light sources is received by the splash guard and transmitted internally to the control panel, where the light that is emitted from the splash guard provides illumination for the user. In another variation, there is provided an electronic patient monitor with one or more light sources affixed thereto, which light sources are used to signal the operating characteristics of the monitor including its alarm volume setting, whether or not it is sounding an alarm, etc. In another variation, there is provided an electronic patient monitor that uses an environmental sensor to adapt its operating characteristics based on conditions proximate to the patient.

33 Claims, 8 Drawing Sheets

U.S. PATENT DOCUMENTS

| | | | |
|---|---|---|---|
| 5,623,760 A | | 4/1997 | Newham |
| 5,633,627 A | * | 5/1997 | Newham ................. 340/573.4 |
| 5,640,145 A | | 6/1997 | Newham |
| 5,654,694 A | | 8/1997 | Newham |
| 5,934,813 A | | 8/1999 | Nyako et al. |
| 5,945,914 A | | 8/1999 | Holmes et al. |
| 5,954,930 A | | 9/1999 | Nafe et al. |
| 5,987,352 A | * | 11/1999 | Klein et al. ................. 600/509 |
| 6,019,481 A | | 2/2000 | Ambach et al. |
| 6,065,727 A | | 5/2000 | Fitzgerald et al. |
| 6,111,509 A | | 8/2000 | Holmes |
| 6,283,602 B1 | | 9/2001 | Kawaguchi et al. |
| 6,292,102 B1 | | 9/2001 | Smith |
| 6,293,683 B1 | | 9/2001 | Okada |
| 6,297,738 B1 | * | 10/2001 | Newham ................. 340/573.1 |
| 6,307,476 B1 | | 10/2001 | Smith et al. |
| 6,417,777 B2 | | 7/2002 | Fitzgerald et al. |

* cited by examiner

APPARATUS FOR LIGHTING A PATIENT MONITOR FRONT PANEL

FIELD OF THE INVENTION

This invention relates generally to monitoring systems and more particularly concerns devices and systems used to monitor seated or lying patients in homes or in medical environments such as hospitals, institutions, and other caregiving environments.

BACKGROUND OF THE INVENTION

It is well documented that the elderly and post-surgical patients are at a heightened risk of falling. These individuals are often afflicted by gait and balance disorders, weakness, dizziness, confusion, visual impairment, and postural hypotension (i.e., a sudden drop in blood pressure that causes dizziness and fainting), all of which are recognized as potential contributors to a fall. Additionally, cognitive and functional impairment, and sedating and psychoactive medications are also well recognized risk factors. In such instances, it is becoming increasingly common to use electronic means to monitor the afflicted patients, with the intent that a nearby (or remote) caregiver will be alerted by the electronics if the patient seeks to rise to his or her feet.

Generally speaking, electronic patient monitors work by first sensing an initial status of a patient, and then generating a signal when that status changes, e.g., he or she has sat up in bed, left the bed, risen from a chair, etc., any of which situations could pose a potential cause for concern in the case of an at-risk patient. Electronic bed and chair monitors typically use a pressure sensitive switch in combination with a separate electronic monitor which conventionally contains a microprocessor of some sort. In a common arrangement, a patient's weight resting on a pressure sensitive mat (i.e., a "sensing" mat) completes an electrical circuit, thereby signaling the presence of the patient to the microprocessor. When the weight is removed from the pressure sensitive switch, the electrical circuit is interrupted, which fact is similarly sensed by the microprocessor. The software logic that drives the monitor is typically programmed to respond to the now-opened circuit by triggering some sort of alarm—either electronically (e.g., to the nursing station via a conventional nurse call system) or audibly (via a built-in siren) or both. Additionally, many variations of this arrangement are possible and electronic monitoring devices that track changes in other patient variables (e.g., wetness/enuresis, patient activity/inactivity, etc.) are available for some applications.

General information relating to mats and electronic monitors for use in patient monitoring may be found in U.S. Pat. Nos. 4,179,692, 4,295,133, 4,700,180, 5,600,108, 5,633, 627, 5,640,145, 5,654,694, and 6,111,509 (the last of which concerns electronic monitors generally). Additional information may be found in U.S. Pat. Nos. 4,484,043, 4,565, 910, 5,554,835, and 5,623,760 (sensor patents) and U.S. Pat. No. 5,065,727 (holsters for electronic monitors), the disclosures of all of which patents are all incorporated herein by reference. Further, co-pending U.S. patent application Ser. No. 09/285,956 (discussing a sensing device which contains a validation circuit incorporated therein) and U.S. patent application Ser. No. 09/944,622, (for automatically configured electronic monitor alarm parameters) are similarly incorporated herein by reference.

Those familiar with the patient monitoring arts will recognize that a typical electronic monitor contains a number of control switches on the top or front thereof. As an example, it is customary to provide switches that reset the unit, that increment or decrement various control parameters (e.g., exit delay time, alarm volume, etc.), that place the unit on hold, etc. Needless to say, it is critical that the caregiver be easily able to read and accurately modify and set these and other parameters. However, this can become problematic in the evening, when the floor lights are intentionally lowered to help the patients sleep. In such a case, the attendants who are charged with checking the status of the electronic monitors at night are faced with the prospect of either turning on the room lights in order to read the display (at the risk of disturbing the patient(s) in the room) or utilizing a flashlight or other light source (which is an added expense, is subject to being mislaid, and requires periodic replacement/recharging of its power source).

Additionally, it is preferable that the volume of the exit alarm that is sounded by the electronic monitor be reduced in volume during the evening and early morning hours. This might be done for many reasons but among the more obvious ones are that the overall noise level of the facility is lower during those times so that the alarm does not need to be heard above as much ambient noise. Further, in the evening it is desirable that patients be allowed to sleep if they are disposed to do so and an unnecessarily loud exit alarm can disturb patients that are housed in the same room or located several rooms distant from the source of the alarm.

However, as desirable as is might be to lower the alarm volume at night it is relatively laborious to individually check each the control panel of each patient monitor in a health care facility to determine whether or not the alarm has been so lowered, and this is especially true in low light conditions. That is, in order to determine the alarm volume of a conventional patient monitor the parameter panel (which might be located, for example, on the front or top of the unit) must be consulted which means a trip across the room, application of illumination to the panel (if it is dark), and, possibly, selection of the appropriate alarm volume parameter from among several parameters in a multi-function display.

Heretofore, as is well known in the patient monitor arts, there has been a need for an invention to address and solve the above-described problems and, more particularly, there has been a need for an electronic patient monitor that has an illuminated control panel for use in low-light conditions. Additionally, there has been a further need for a way to easily determine whether or not a patient monitor has been set into low-volume mode, and this is especially true when that determination needs to be made in low-light conditions. Accordingly, it should now be recognized, as was recognized by the present inventors, that there exists, and has existed for some time, a very real need for a system for monitoring patients that would address and solve the above-described problems.

Before proceeding to a description of the present invention, however, it should be noted and remembered that the description of the invention which follows, together with the accompanying drawings, should not be construed as limiting the invention to the examples (or preferred embodiments) shown and described. This is so because those skilled in the art to which the invention pertains will be able to devise other forms of this invention within the ambit of the appended claims.

SUMMARY OF THE INVENTION

In accordance with a first aspect of the instant invention, there is provided an electronic patient monitor that is equipped with a "splash guard" or similar covering of the monitor control panel, which indirectly lights its controls so that they can be read in low light settings. Additionally, and in another preferred embodiment, the color or intensity of the illuminating light changes, preferably at about one-half second time intervals, during the time when the alarm is sounding. In still another preferred arrangement, the indirect lighting is used as an indicator to signal when the alarm volume has been reduced as might be done during the evening hours. By varying the intensity and/or color of the illuminating light, the instant invention makes it possible for the caregiver to quickly determine at a glance whether or not the volume of the alarm has been (or should be) reduced.

Turning now to a first preferred embodiment of the instant invention, there is provided hereinafter an apparatus for indirectly lighting the control panel of an electronic patient monitor. By "indirect" lighting, the instant inventors mean that one or more light sources (preferably LEDs) are positioned on the body of the electronic monitor and oriented so that their light does not fall directly on the control panel. Instead, the control panel receives illumination from these lights via internal conduction through a "light pipe" or other optically conductive material. In the preferred embodiment, a splash guard or similar utilitarian structure functions as the light pipe and transmits light from LEDs that have been positioned on the rear of the unit, up and over the top of the body of the monitor, where the light is emitted to illuminate the electronic monitor top panel.

According to another preferred arrangement, a lighting system is taught that utilizes the illuminating light intensity and/or light color as a signal to the caregiver that the bed (chair, etc.) alarm has been triggered and the alarm is sounding. By way of explanation, in a hospital ward it may be difficult in low light conditions to determine which alarm is sounding among many possible sources of that alarm. Additionally, it can be difficult to even locate the patient monitor in a single room when the lights are low, as it is possible for it to be obscured by equipment, bed clothes, etc. However, in the preferred embodiment the sounding alarm will be accompanied by a flashing or other time-variable activity (or change of illuminative state) of the indirect lighting system, said flashing taking the form of alternating colors and/or alternating light intensities. In the preferred embodiment, the lighting system will be the indirect lighting system discussed above.

According to still another preferred embodiment, there is provided hereinafter an indirect lighting system substantially as described above, but wherein the indirect lighting system is preferably used to signal whether or not the electronic monitor alarm has been set to a low volume. Thus, in the preferred embodiment the lighting system will be utilized in such as way to inform the caregiver in at least a general way of the volume level of the unit. According to one preferred arrangement, the intensity of the lighting will be varied depending on whether the alarm volume is "loud" or "soft", with a "brighter" illumination preferably being used when the volume is set to low volume. In other preferred variations, the color (e.g., red might correspond to low volume, and yellow to high volume, etc.) of the illuminating lighting will be varied depending on the volume level, thereby allowing a nurse or other caregiver to determine at a glance whether or not the alarm volume has been reduced.

Finally, there is also provided an electronic patient monitor, wherein the monitor's operating characteristics are adaptable to conform to the environment of the patient. According to a first preferred embodiment, the electronic patient monitor is equipped with a photo-sensitive electronic device for measuring the ambient light in the patient's room. Depending on the measured light level, the electronic monitor would preferably activate one or more light sources during the time when the patient room is dark and deactivate those same lights when the patient's room is lighted. In another preferred arrangement, the electronic patient monitor will automatically change the volume of its alarm in response to changes in the ambient light in the room, with the volume decreasing during period when the room is dark and increasing during daylight hours. In another preferred arrangement, the operating characteristics of the monitor are changed in response to the time of day.

The foregoing has outlined in broad terms the more important features of the invention disclosed herein so that the detailed description that follows may be more clearly understood, and so that the contribution of the instant inventor to the art may be better appreciated. The instant invention is not to be limited in its application to the details of the construction and to the arrangements of the components set forth in the following description or illustrated in the drawings. Rather, the invention is capable of other embodiments and of being practiced and carried out in various other ways not specifically enumerated herein. Further, the disclosure that follows is intended to apply to all alternatives, modifications and equivalents as may be included within the spirit and scope of the invention as defined by the appended claims. Finally, it should be understood that the phraseology and terminology employed herein are for the purpose of description and should not be regarded as limiting, unless the specification specifically so limits the invention.

While the instant invention will be described in connection with a preferred embodiment, it will be understood that it is not intended to limit the invention to that embodiment. On the contrary, it is intended to cover all alternatives, modifications and equivalents as may be included within the spirit and scope of the invention as defined by the appended claims.

BRIEF DESCRIPTION OF THE DRAWINGS

Other objects and advantages of the invention will become apparent upon reading the following detailed description and upon reference to the drawings in which.

DETAILED DESCRIPTION OF THE INVENTION

According to a preferred aspect of the instant invention, there is provided an electronic monitor for use with a patient sensor, wherein the monitor's control panel is indirectly illuminated through the use of light-conducting materials. In other embodiments, the light that illuminates the control panel is used for other purposes, such as to signal the alarm volume level and to indicate when the alarm is sounding.

General Background

By way of general background, in a typical arrangement, a typical pressure-sensing mat suitable for use with the electronic patient monitor discussed herein is a sealed "sandwich" composed of three layers: two outer layers and an inner (central) layer positioned between the two outer layers. The outer layers are usually made of some sort of plastic and are impermeable to fluids and electrically non-conductive on their outer faces, where "outer" is determined with respect to the middle layer. The inner surface of each of the outer layers—which inner surfaces are oriented to face each other from opposite sides of the central layer—is made to be electrically conductive, usually by printing a conductive (e.g., carbon-based) ink on that surface. The compressible middle "central spacer" is made of a non-conductive material and serves to help keep the two conductive faces apart when a patient is not present on the sensor. The central spacer is discontinuous, which makes it possible for the two conductive inner surfaces to be forced into contact through the one or more discontinuities when weight is applied to the switch. By attaching a separate electrical lead to each of the conductive inner faces, it can readily be determined via a simple continuity (or low voltage) check whether a weight is present on the sensor (e.g., a patient is seated thereon). Removal of the weight causes the central spacer to expand and press apart the two conducting faces, thereby breaking the electrical connection between them. Thus, a device that monitors the resistance across the two electrical leads may determine when a patient has moved from a seated or prone position.

That being said, the instant invention is suitable for use with a wide variety of patient sensors in addition to pressure sensing switches including, without limitation, temperature sensors, patient activity sensors, toilet seat sensors (see, e.g., U.S. Pat. No. 5,945,914), wetness sensors (e.g., U.S. patent application Ser. No. 09/596,268), decubitus ulcer sensors (e.g., U.S. patent application Ser. No. 09/591,887), etc. Thus, in the text that follows "mat" or "patient sensor" should be interpreted in its broadest sense to apply to any sort of patient monitoring switch, whether the sensor is pressure sensitive or not.

Figure 1:
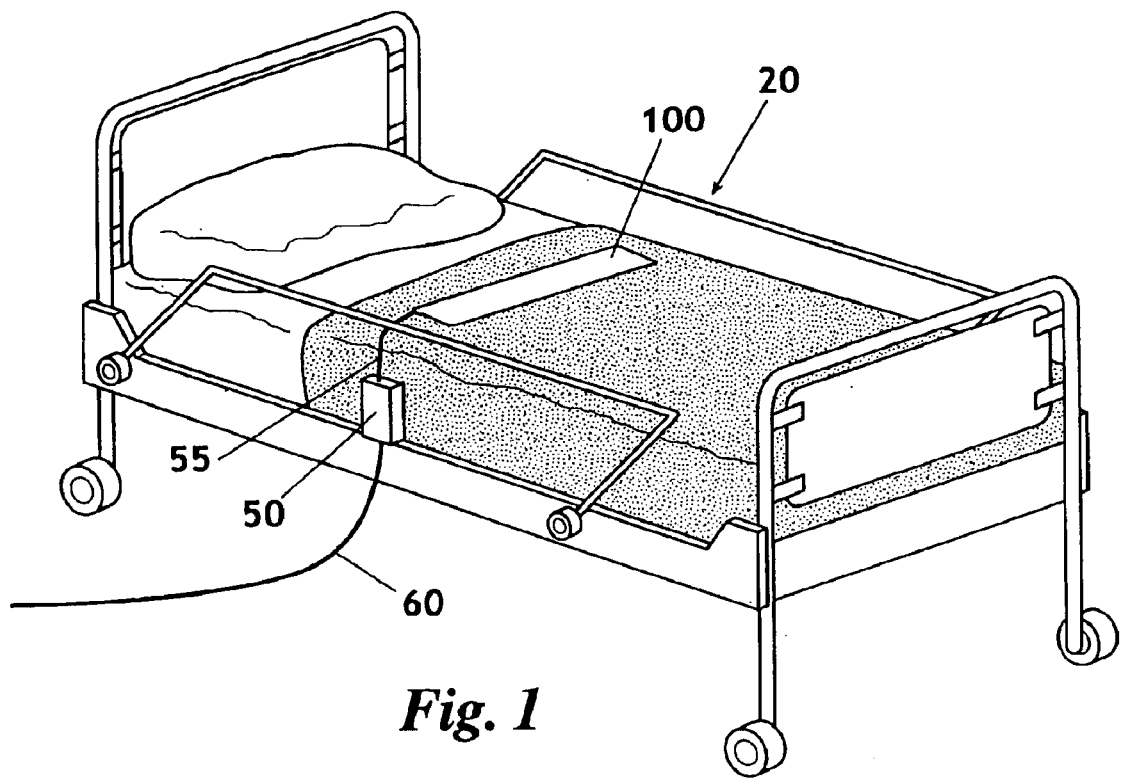
FIG. 1 illustrates the general environment of the instant invention, wherein an electronic patient monitor is connected to a bed mat.

Turning now to FIG. 1 wherein the general environment of the instant invention is illustrated, in a typical arrangement a pressure sensitive mat 100 is placed on a hospital bed 20 where it will lie beneath a weight-bearing portion of the reclining patient's body, usually the buttocks and/or shoulders. Generally speaking, the mat 100/electronic monitor 50 combination works as follows. When a patient is placed atop the mat 100, the patient's weight compresses the mat 100 and closes an electrical circuit, which closure is sensed by the attached electronic patient monitor 50. When the patient attempts to leave the bed, weight is removed from the sensing mat 100, thereby breaking the electrical circuit, which interruption is sensed by the attached electronic patient monitor 50. The patient monitor then signals the caregiver per its pre-programmed instructions. In some cases, the signal will amount to an audible alarm or siren that is emitted from the unit. In other cases, an electronic signal could be sent to a remote nurses/caregivers station via electronic line 60. Note that additional electronic connections not pictured in this figure might include a monitor power cord to provide a source of AC power—although, as generally pictured in this figure, the monitor 50 can certainly be configured to be either battery or AC powered.

Figure 2:
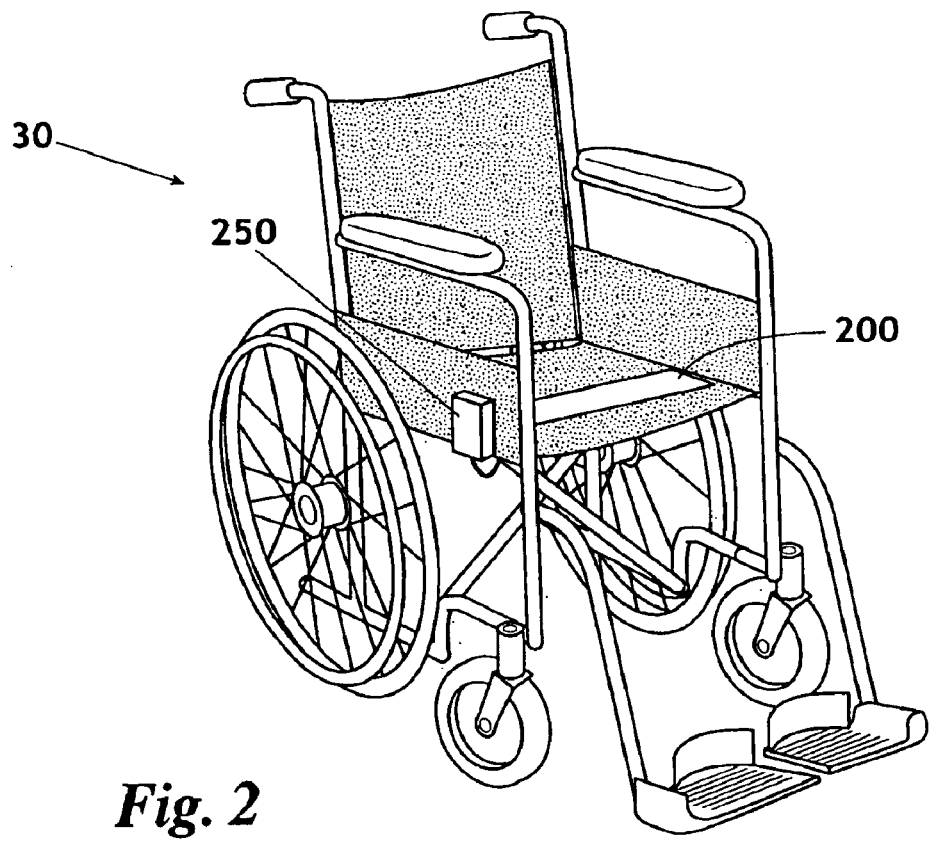
FIG. 2 illustrates the general environment of the instant invention, wherein an electronic patient monitor is connect to a chair mat.

In another common arrangement, and as is illustrated in FIG. 2, a pressure sensitive chair sensor 200 might be placed in the seat of a wheel chair or the like for purposes of monitoring a patient seated therein. As has been described previously, a typical configuration utilizes a pressure sensitive mat 200 which is connected to electronic chair monitor 250 that is attached to the chair 30. Because it is anticipated that the patient so monitored might choose to be at least somewhat mobile, the monitor 250 will usually be battery powered and will signal a chair-exit event via an internal speaker, rather than a nurse-call interface.

Turning now to the particular circumstances in which the instant invention would be most useful, as is well known to those of ordinary skill in the art it can be difficult in a darkened room to locate, read, and manipulate the control panel of a bed-exit monitor. Further, identifying which alarm is sounding among the many that might be present in a darkened room can be a frustrating task. For example, in some cases there may be several patients in a room, only one of which is fitted with an exit monitor. In other cases, the patient may have attempted to circumvent the electronic monitor by unplugging the mat which can, depending on the programming of the monitor, trigger a "pull out alarm." Of course, if patient then quickly puts his or her head back down on the pillow, the nurse will be unable upon entry into the room which bed needs attention, and this is especially true in a darkened room.

Preferred Embodiments

Figure 3:
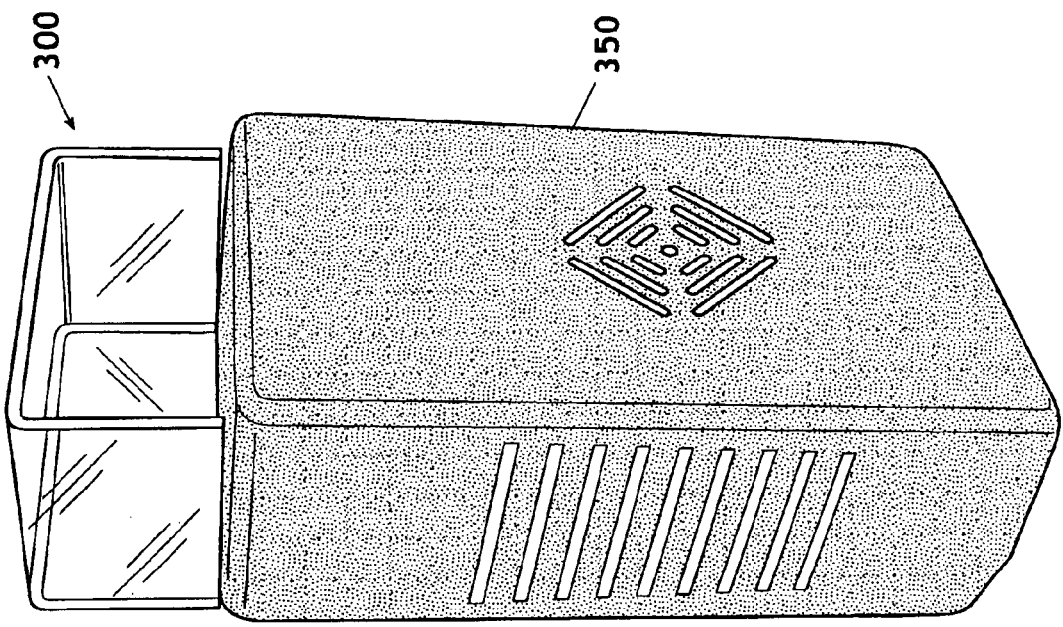
FIG. 3 contains a schematic drawing of a preferred monitor/splash guard arrangement.

Turning now to a detailed discussion of the various aspects of the instant invention 300, FIG. 3 illustrates a first preferred embodiment wherein an electronic patient monitor 350 is surmounted by a splash guard 300 which provides indirect illumination to light the control panel 600 that is protected thereby. The splash guard 300 preferably has an open front face (best seen in FIG. 6) which allows a user to access the electronic monitor control panel 600 which is conventionally located on the top of the unit. That being said, it should be clear to those of ordinary skill in the art that whether the control panel 600 was located on the top, bottom, front, or side of the monitor 350, a similar arrangement could be developed.

The splash guard 300 is preferably made of a transparent or translucent material such as polycarbonate. Polycarbonate is especially suitable for use in the instant invention because of its ability to act as a light conduit (or light pipe) as is described more fully below. That being said, any transparent or translucent material might be used so long as its index of refraction is greater than that of air so that it transmits sufficient light internally to be useful for the purposes discussed below.

Figure 4:
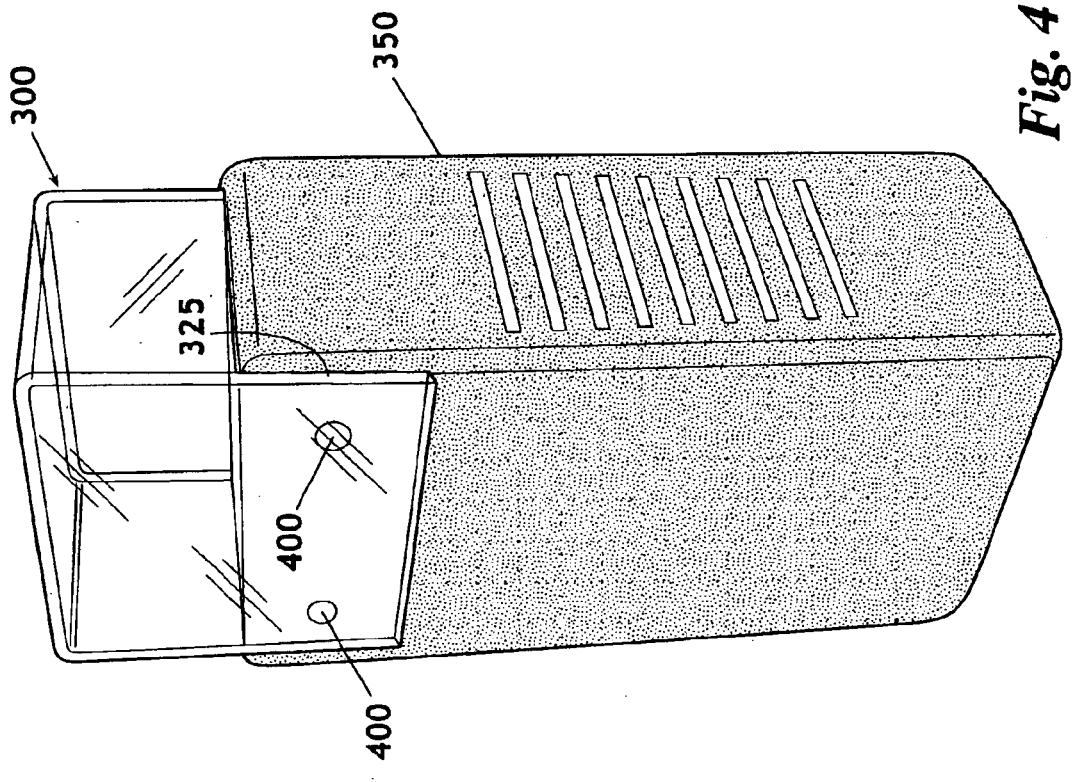
FIG. 4 is a schematic illustration of the rear surface of a preferred monitor/splash guard embodiment which illustrates more clearly how the light sources are preferably positioned when the control panel is located on the top of the unit.
Figure 5:
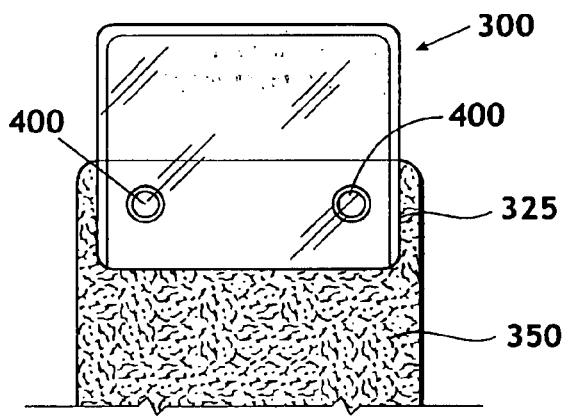
FIG. 5 contains a view of the upper portion of the rear of a preferred monitor/splash guard embodiment.
Figure 6:
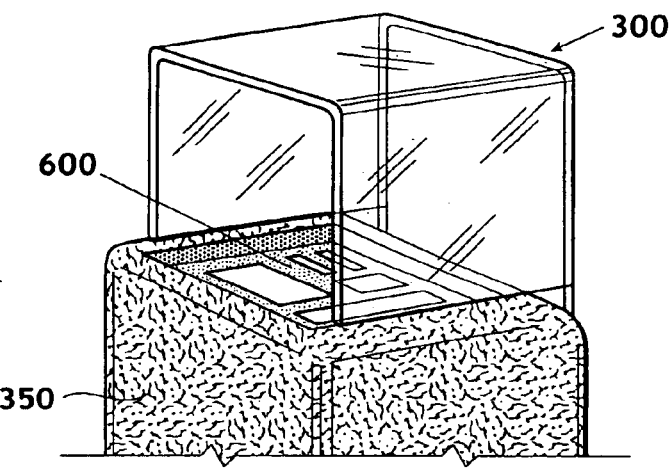
FIG. 6 contains a schematic illustration of a preferred monitor/splash guard arrangement which illustrates more clearly how the splash guard protects and illuminates the control panel.

The principle improvement of the splash guard 300 of the instant invention over the prior art is that it is configured to conduct light from one or more remotely positioned light sources 400 on the monitor 350 via internal reflection (i.e., it acts as a "light pipe") to the top of the monitor 350, where escaping light indirectly illuminates the control panel 600. As can be seen in FIGS. 4, 5, and 6, in the preferred arrangement the light sources 400 are positioned on the back of the monitor 350 where they do are generally directed away from the control panel 600 and, hence, do not directly illuminate it. That being said, it should be clear that the light sources 400 could positioned on the front of the monitor 350, on one or both sides, or any other place on the monitor 350 where the light therefrom can radiate on the splash guard 300 for transmission to the control panel 600.

Additionally, the back panel of the splash guard 300 is preferably extended down the rearward surface of the monitor 350. This feature has two functions. First, the downward extension 325 provides a means for mechanically attaching the splash guard 300 to the monitor 350 (e.g., by inserting screws—not shown in the figures for purposes of clarity—through the downward extension 325 and into the monitor case 800 or by adhering it to the monitor 350 exterior with some sort of adhesive). A second and more critical function of the downward extension 325 of the splash guard 300 is to bring it into contact with light sources 400 have preferably been inserted through the monitor case 800 and extend at least a small distance beyond it.

Figure 7:
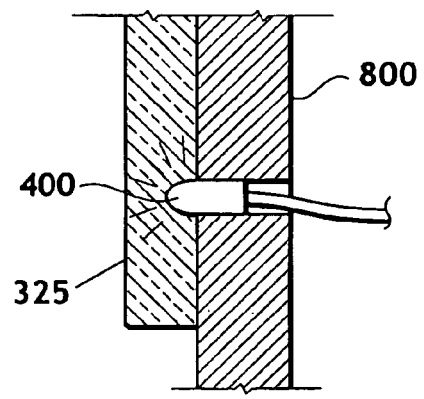
FIG. 7 illustrates a preferred arrangement wherein the source of illumination penetrates at least partially into the interior of the splash guard back plate.

As is best illustrated in FIG. 7, in the preferred embodiment at least a portion of a light source 400 extends beyond the surface of the monitor case 800 and at least some small distance into the downward extension 325 of the splash guard 300. One purpose which is served by extending the light source 400 at least partially into downward extension 325 is to improve the efficiency of the transmission of light into the interior of the splash guard 300. Those of ordinary skill in the art will recognize that by inserting the light 400 some distance into the interior of the splash guard 300 a greater proportion of the light emitted from the light source 400 will potentially be trapped therein, which ultimately increases the amount of light that will be emitted in proximity to the control panel 600. That being said, it is not an essential aspect of the instant invention that the light source 400 be so inserted and this arrangements has been suggested only because the instant inventors have found that doing so results in an improved product.

Figure 8:
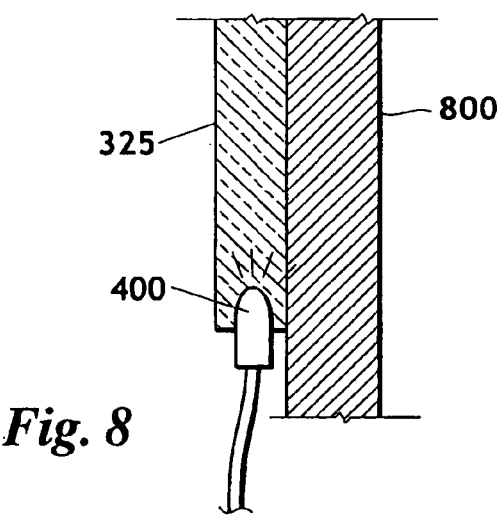
FIG. 8 illustrates another preferred arrangement, wherein the light source penetrates an edge of the back plate.

In another preferred arrangement, the light source 400 is configured to be inserted into the material of the splash guard 300 via one of its edges. FIG. 8 illustrates an arrangement wherein the light source 400 is inserted into the bottom edge of extension 325. Obviously, any edge might be utilized, although the preferred arrangement is to use the bottom edge. As has been noted previously, inserting the light source 400 into the material of the splash guard has been done to improve the amount of light trapped therein and is not an essential feature of the instant invention.

Preferably the splash guard 300 will be molded of a single piece of polycarbonate plastic to increase the amount of light that is delivered to the control panel 600. By way of explanation, it should be clear to those of ordinary skill in the art that if the splash guard 300 is created by joining together multiple pieces, each joint will tend to reflect a portion of the light that travels through that interface, thereby reducing the amount of light that is delivered to the control panel 600. Hence, in the preferred embodiment the splash guard will be created as a single piece without joints, seams, or other discontinuous regions.

According to another preferred embodiment of the instant invention, there is provided an electronic patient monitor, wherein the light that illuminates the control panel is used to indicate different aspects of the operating characteristics of the electronic monitor 350. Note that, in the preferred embodiment, the indirect illumination system disclosed above will be utilized. However, those of ordinary skill in the art will recognize that the invention that is described below could be used with either direct or indirect lighting.

According to a first embodiment, the lights 400 are used to indicate when the volume of the electronic monitor has been set to a "low" level, where the particular volume level corresponding to "low" is defined by the manufacturer and/or user. This configuration provides a way for the caregiver to determine at a glance whether the alarm volume has been lowered for the evening, and this determination can readily be made in low-light settings. Note that it is traditional to allow the user to set the alarm volume of the patient monitor 350 manually, either via a switch within control panel 600 or located elsewhere. Further, the user might be offered various alternatives with respect to the way in which the alarm volume is changed including, using a switch to toggle the alarm volume between high and low (two preset values); adjusting the alarm volume in discrete steps over some range (e.g., volumes from "0" to "9"); or continuously varying the volume using a wheel or similar mechanism, etc. Exactly how the volume is set is a design choice that is well within the ability of one of ordinary skill in the art to devise.

Preferably, the CPU 900 will be programmed to increase the intensity of the illuminating lights 400 as the alarm volume is decreased. Whether the increase in light intensity is gradual with each decrease in volume, or whether there is a threshold volume value that causes the light intensity to increase markedly, is a matter of choice for the designer and those of ordinary skill in the art will readily recognize how to implement either. Additionally, in the preferred arrangement the lights 400 will be turned off completely when the electronic monitor 350 is set to a "high" volume, the assumption being that it is daylight. Obviously, there are many circumstances when this might not be the case so it would be preferable to allow the user to override (e.g., in a dark but noisy environment).

Figure 9:
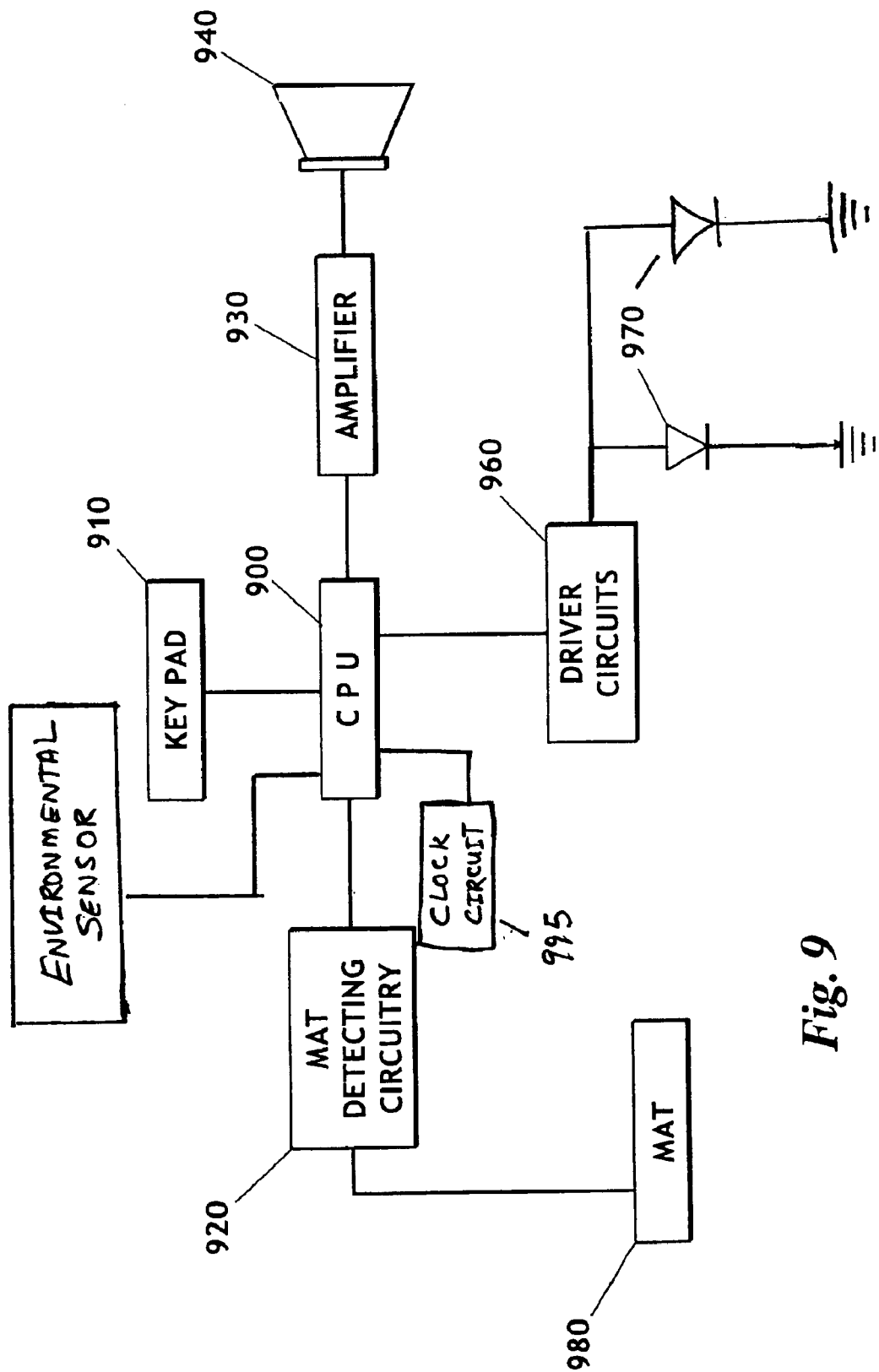
FIG. 9 contains a hardware schematic of a preferred embodiment of the instant invention, wherein the light sources are used to provide a visual indication of the relative alarm volume that the user has selected.

Turning next to FIG. 9 wherein a preferred electronic monitor hardware configuration is illustrated, the CPU 900 is situated so as to be able to detect changes in an attached patient sensor 980, such as a pressure sensitive mat, via mat detection circuitry 920. It also preferably will be in electronic communication with, and programmed to monitor the status of, keypad circuitry 910, which is designed to provide a way for a user to communicate with the internal programming of the monitor (e.g., the outward manifestation of keypad circuitry 910 would be the switches that make up the operating portion of control panel 600). The amplifier 930/speaker 940 circuit is preferably configured to allow the microprocessor 900 to synthesize the audio alarms that are heard through the speaker 940, thereby providing allowing the end-user greater choice in the selection of alarm sounds. Note that the amplifier 930 may not be necessary in some cases, and this is especially so where the speaker 940 is a piezoelectric device. Of course, the entire system will need some source of electrical power, not pictured, to supply power to the components of FIG. 9, and it is immaterial as to whether that source is AC or DC. Although not illustrated in FIG. 9, in many cases the electronic monitor will contain circuitry for interfacing with the facility nurse call system and the inclusion of such circuitry as part of the embodiment of FIG. 9 is well within the ability of one of ordinary skill in the art.

Additionally, a light driver circuit 960 is also preferably provided which activates LED 970 under direction of the microprocessor 960 in accordance with its internal programming. Depending on the particular driver 960 employed and the desires of the designer, there may be multiple LEDs 970 that are controlled by a single driver 960 or multiple driver circuits 960 that are all under the control of the CPU 900. Those of ordinary skill in the art are certainly capable of implementing a variety of different variations of this basic idea.

In operation, light that enters the splash guard 300 from the light source 400 will be at least partially trapped within the confines of the material of the splash guard 300 and will travel internally through that material upward and around its upper extent, where it will be emitted proximate to the control panel 600. In FIG. 5 it is made clear that light source 400 preferably penetrates into the interior of the splash guard back plate, so that light is efficiently transmitted into the interior thereof. Such light then travels upward through the back plate and is radiated from the sides and top of the splash guard 300, thereby providing an illumination sufficient to enable the caregiver to read the top panel 600 in low-light conditions.

In another preferred arrangement, the light source is positioned at the bottom edge of the splash guard 300 (e.g., light source 325 in FIG. 5).

Light source 400 is preferably a light emitting diode (LED), but obviously the type of light source is not critical to the operation of the instant invention and it could instead be incandescent, fluorescent, cold cathode, electroluminescent, etc. Additionally, and as described above, multi-color LEDs and/or multiple LEDs of different colors could also be used and, for some applications as described below, might be preferable.

It is critical for purposes of the instant embodiment that the lighting source of the top panel be indirect, i.e., that light be transmitted internally within the splash guard 300 from a remote light source 400 to illuminate the control panel 600 and should be distinguished from direct front lighting, or direct back lighting, of the control panel 600. Note that this implies that the instant invention 300 would then preferably be molded from a single piece of polycarbonate in order to maximize the amount of light that is conducted internally, as joining together different pieces would most likely severely reduce the amount of light that is transmitted to the top panel 600.

Note that it is not essential that the splash guard 300 be rectangular in shape, nor that it completely enclose the top panel 600. As an example, the upper-most surface of the splash guard 300 could be curved instead of rectangular. Similarly, the side panels of the splash guard 300 are optional, as light that is from the top surface would be sufficient in most cases. Finally, in still another embodiment, only the side and rear panels of the splash guard 300 might be used (i.e., splash guard 300 without the upper-most surface), thereby creating a variant with an open "top".

Second Aspect

In another preferred arrangement, the light sources 400 are utilized to indicate that the alarm of the patient monitor 150 has been placed in low-volume mode. Preferably, setting the alarm to a lower volume will automatically activate the light sources 400. The advantage of this arrangement is that it enables a caregiver to tell from across the room whether or not the alarm has been set to low volume for night time use.

As is generally illustrated in FIG. 9, in a preferred arrangement the electronic patient monitor 350 will be controlled by a microprocessor 900 or similar programmable device which is in electronic communication with the various peripheral devices that would normally be used in a patient monitoring environment. For example, mat detection circuitry 920 is preferably situated between the CPU 900 and the mat 980 (or other patient sensor) and would be typically used by the CPU 900 to determine whether or not a sensor is attached thereto. Keypad 910 might be a conventional membrane switch or other input device that is configurable to accept operating parameter values from the user. CPU 900 is also preferably used to synthesize various alarm sounds under software control, with the output being preferably fed in to amplifier 930 and then subsequently on to speaker 940. Of course, the electronic device of FIG. 9 will necessarily require some sort of power, whether AC or DC. Finally, CPU 900 is preferably connected to driver circuit 960 and ultimately on to LED 970, the purpose of which circuit is to allow the CPU 900 to control the time when the LED 970 is illuminated as is described below. The driver circuit 960 might control a single LED or multiple LEDs according to the wishes of the designer. Additionally, it is certainly possible that multiple driver circuits 960 might be utilized, each separately controlling one or more LEDs 970 under the direction of the CPU 900.

Figure 10A:
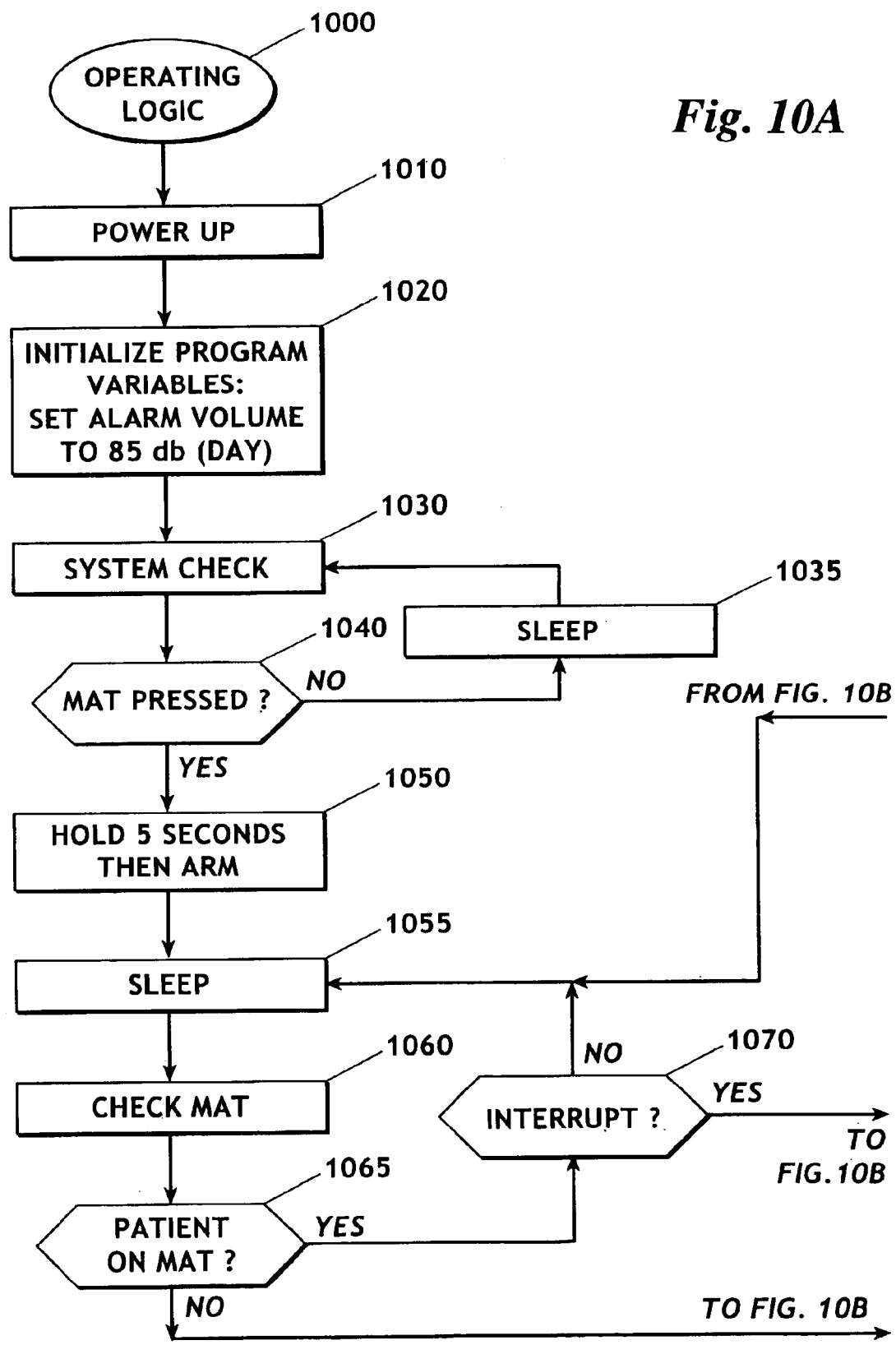
FIG. 10 illustrates a preferred computer software logic for utilizing the light sources as visual indicators of relative alarm volume.
Figure 10B:
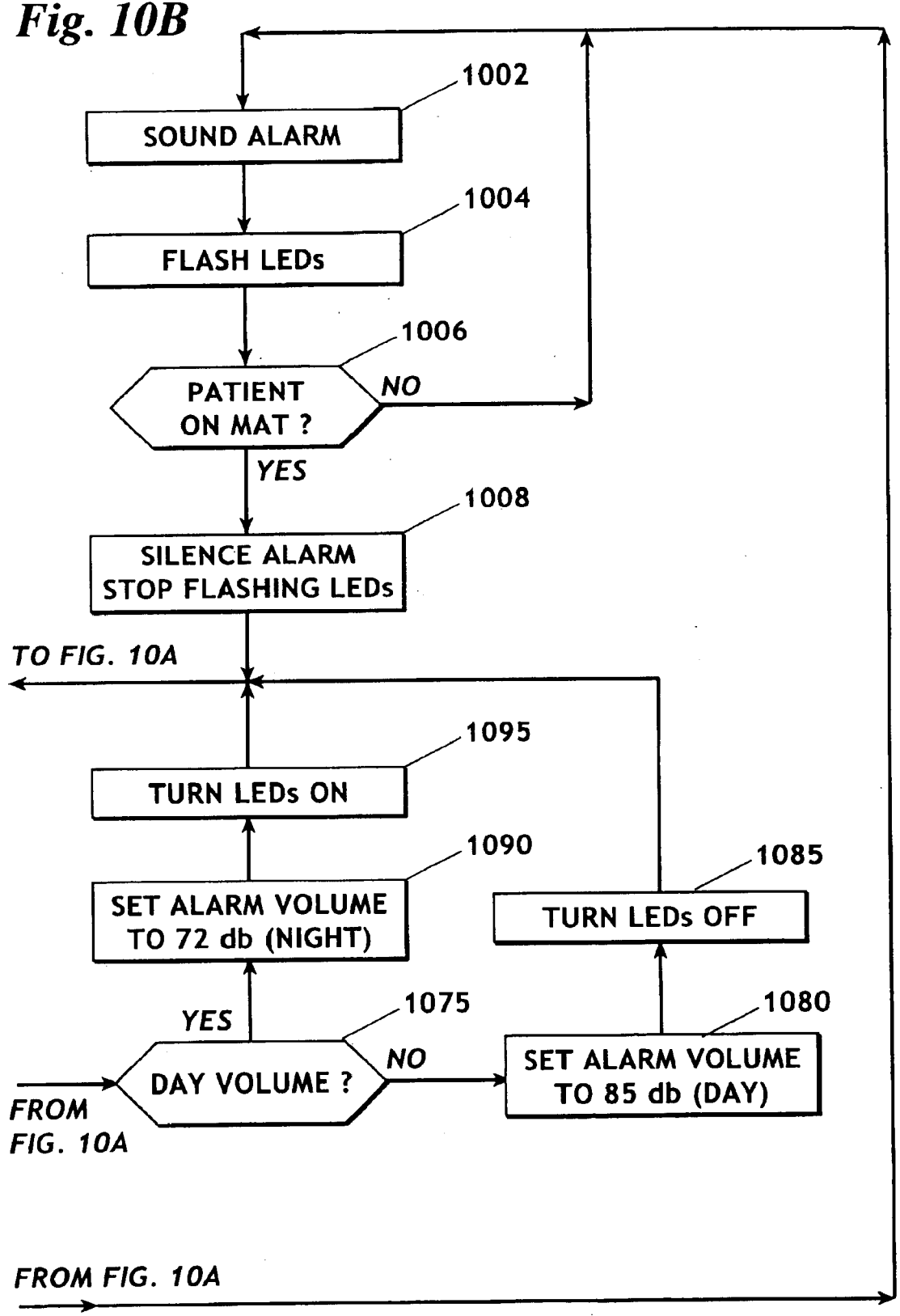

In a preferred arrangement, software that is contained either partially or entirely within the CPU 900 will operate generally according to the flow diagram of FIG. 10. When the unit is powered up 1010, an number of initialization steps will take place 1020 including setting the alarm volume parameter to a "day" level, which in the currently preferred arrangement would yield a speaker volume of about 85 db, as compared with a "night" speaker volume level of about 72 db. Preferably, the "day" and "night" alarm volume parameters will be maintained in non-volatile memory of some sort, so that these levels can be restored if power is removed from the monitor for whatever reason. It should be clear that the precise sound volume level in each situation is one that would normally be a design decision and might be made to be at least somewhat adjustable according to the user's preferences.

Next, and according to the preferred arrangement, the instant monitor would normally perform at least a minimal system check 1030, which might include such functions as checking to see whether a patient sensor (e.g., a pressure sensitive mat) is attached thereto and properly functioning. Assuming that the check was successful, as a next preferred step it will be next determined whether the attached mat

1040 is pressed or, in the case of other sorts of patient sensors, whether the sensor is engaged/activated.

In the event that the software determines that the mat is pressed, it would typically set the unit to hold mode 1050 for a period of about five seconds, after which the unit would arm itself. Preferably, the CPU would next enter an event loop that alternately puts the microprocessor to sleep 1055 (in order to conserve battery power, if the monitor is so powered), wakes it, checks the attached mat 1065 to see if the patient is still present, and then puts the CPU back to sleep 1055 if the patient's status is unchanged.

Preferably, the interrupt circuitry of the microprocessor will be used to allow the user will to toggle the volume of the alarm between "day" and "night" levels. As is illustrated in FIG. 10, in one preferred embodiment if an interrupt 1070 is received (e.g., if the caregiver presses the appropriate switch) during the main event loop, the program logic determines 1075 whether the alarm volume parameter is currently set to its higher "day" level. If that determination is "true", the software preferably switches the alarm level parameter to a lower volume level 1090 which corresponds to night usage. If, on the other hand, the volume parameter is currently set to a value corresponding to night usage, the alarm volume is toggled to a "day" level 1080. After these adjustments, the monitor preferably returns to monitoring via the main even loop. Those skilled in the art will recognize that a microprocessor "interrupt" need not be processed sequentially, but can instead cause the microprocessor to immediately "jump" to a new section of code. However, for purposes of the instant discussion, it will be assumed that interrupts are "handled" by the code and that they are processed as disclosed according to the program logic FIG. 10.

Finally, although there are any number of ways to control the alarm volume the instant inventors prefer that it be controlled by varying the pulse width of the signal that is generated by CPU 900. In more particular, preferably the CPU 900 will be used to synthesize the alarm sounds that are sounded through the attached speaker 940. General methods of synthesizing alarms sounds are well known to those of ordinary skill in the art (e.g., Fourier synthesis, voice synthesis, digital voice playback, and many others). In brief, such methods generally operate by creating time-varying voltage changes—usually in the form of a series of square waves—on one of the output pins of the microprocessor 900, wherein the frequency with which the square waves are presented to amplifier 930 controls the pitch of the resulting sound and its character. Of course, as a general matter if the amplitude of the square or other wave series is increased or decreased the volume of the sound emitted via the speaker 940 will be similarly changed. Additionally, however, the instant inventors have determined that the level of the output speaker 940 volume may be controlled by varying the pulse width (as opposed to amplitude, etc.) of the square wave series, with wider pulse widths corresponding to louder alarm volumes. Within a fairly broad range of pulse widths, wider pulse widths produce a louder speaker volume. In the preferred arrangement, PWM (i.e., pulse width modulation) will be used to control the volume of the speaker, although other digital modulation amplification techniques might also be used including pulse frequency modulation, pulse frequency modulation, pulse modulation amplification, pulse step modulation, pulse amplitude modulation, pulse position modulation, pulse time modulation, etc.

According to another preferred embodiment, and as is generally illustrated in FIGS. 9, 10, 11, and 12, there are provided an electronic patient monitors 1110 and 1200 substantially similar to that discussed previously, but wherein the LEDs are utilized to communicate the speaker volume level and/or the alarm status to the attendant caregiver. In more particular, the light sources 400/1110/1220 will preferably be automatically turned "on" 1095 when the alarm volume is set to a "low" level (corresponding to night), and turned "off" 1085 when the alarm volume is increased to its louder day setting. Those of ordinary skill in the art will recognize that many different variations of this theme might be utilized including, for example, changing the color of the light as the alarm volume is changed, changing the brightness or intensity of the light as the volume is changed (as opposed to completely shutting off the light source at high volume), etc. Of course, in the preferred arrangement the CPU 900 will control whether or not the light sources 400 are activated and the intensity/color of the light emitted thereby. That being said, it is not essential that a microprocessor be involved in this process and those skilled in the art are easily able to devise analog circuits to yield the same functionality.

According to still another preferred embodiment, there is provided an electronic patient monitor substantially similar to that described above, but wherein the light sources 970 are used to provide a visual indication that the alarm is sounding. As is indicated in FIG. 10, the instant embodiment is preferably implemented under microprocessor control, although other arrangements are certainly possible. Step 1002 is reached when the patient monitor is armed and the patient's status changes (e.g., the patient leaves the mat). In such a case, the CPU 900 will sound the alarm 1002 locally and/or remotely via a nurse call or similar arrangement. Additionally, though during the time that the alarm is sounding, the microprocessor will preferably repeatedly turn the one or more light sources 970 on and off (flash 1004), and/or alternate the colors of the light sources 400 (e.g., if a multi-color LED is used) until the patient returns to the mat (patient check 1006), the alarm is manually silenced 1008 by the caregiver (e.g., by pressing "reset" or some other button on the control panel), or the siren is terminated for other reasons under software control. The previous examples of varying the characteristics of the light sources during the time the alarm is sounding (i.e., flashing and displaying alternate colors) and any other time-varying lighting effects will be referred to generally hereinafter as changing the current illuminative state of the light.

Figure 11:
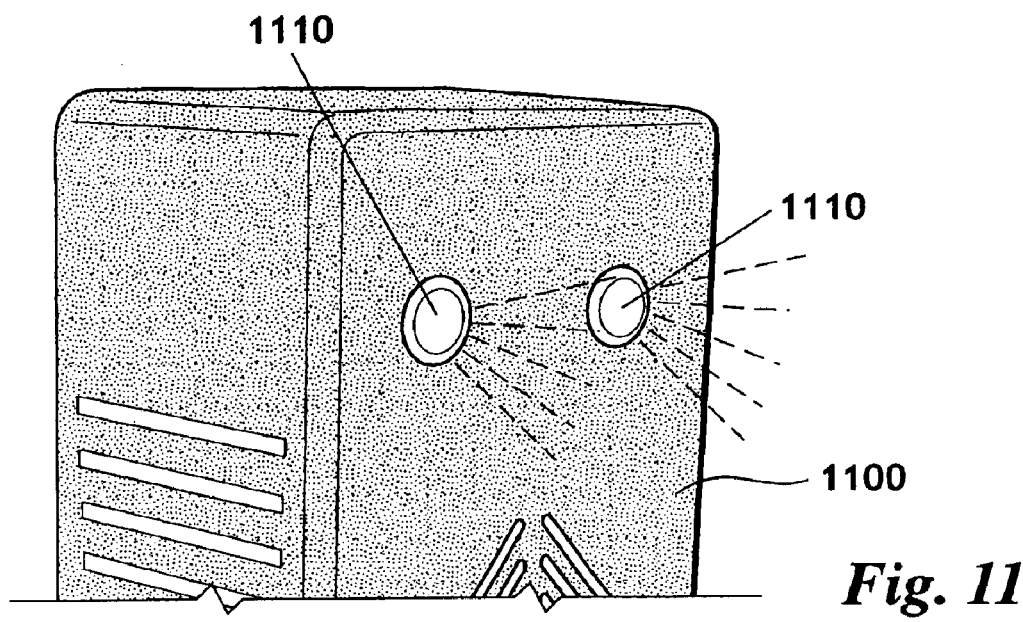
FIG. 11 contains another preferred embodiment, wherein light sources are positioned on the front of the electronic monitor.
Figure 12:
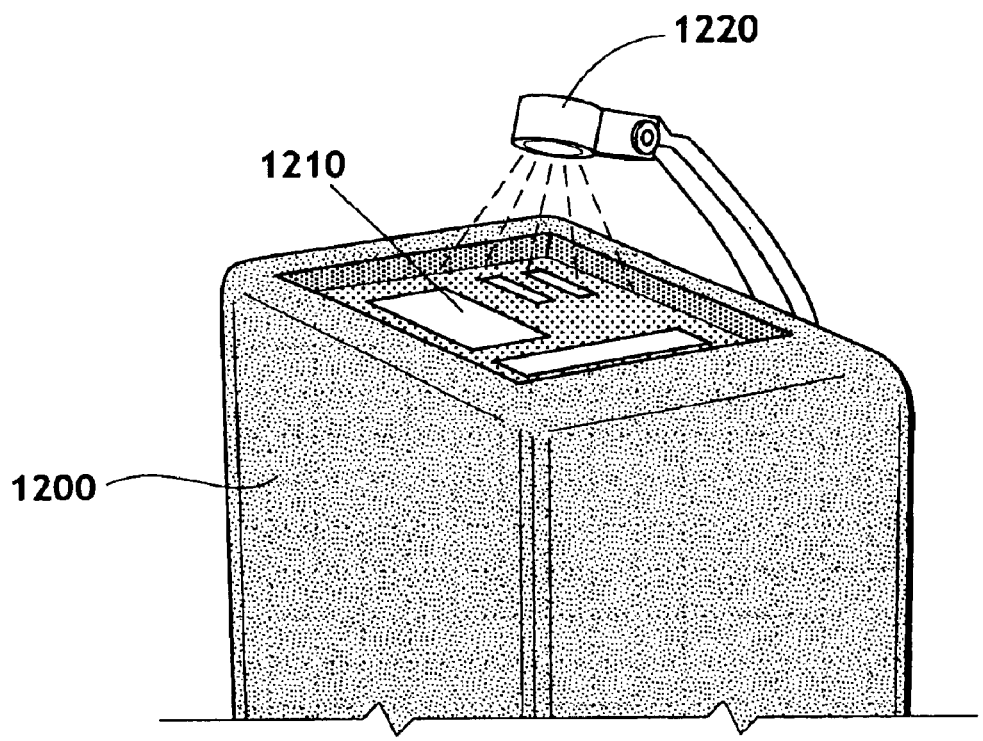
FIG. 12 illustrates another preferred arrangement, wherein the light source is positioned above the control panel.

As should be made clear from FIGS. 11 and 12, in the last two embodiments it is not essential that the light sources 1110 and 1220 be proximate to splash guard 300, as the lights in these configurations are acting to signal various conditions of the monitor 1100 and 1200. Indeed, these light sources 1110 and 1220 could also be used in addition to the light sources 400 of FIG. 4. Similarly, the light sources 400 could be used in a signaling capacity, thus the embodiment of FIGS. 3 through 7 could readily be made to function according to the embodiments discussed just previously. Further, and as should be made clear by FIGS. 11 and 12, the light sources 1110 and 1220 need not be located at any particular place on the monitor but instead can be positioned wherever it makes the most sense, although light source 1220 would preferably be positioned where it could shed light on control panel 1210. Finally, the light sources 1110 could also be integrated into or made a part of the control panel 600.

In another preferred arrangement, the instant inventors have developed an electronic patient monitor that automatically changes the illuminative state of one or more of its light sources in response to changes in some environmental quantity. According to the preferred embodiment of FIGS. 9 and 13, it is contemplated that an environmental sensor 990 will be placed into electrical communication with the CPU 900 and positioned within the monitor case (or external to it) so as to be able to sense some environmental variable. For example, one of the light sources 1110 might be replaced by such a sensor 990, thereby giving the sensor 990 direct access to the external environment of the monitor 1100. Values read from the environment by the sensor would be communicated to the CPU 900 continuously or periodically and the illuminative state of the light sources 400/1110/1220 would be varied according to the programming of the patient monitor and/or according to its particular hardware design.

In a first preferred arrangement, there is provided a an electronic patient monitor as described above, but wherein the intensity and/or color of the light sources 400, 1100, or 1220 is automatically changed depending on the level of the ambient light. In the embodiment of FIG. 9, it is preferred that a photo-sensitive circuit—environmental sensor 990—be provided on the exterior of the case 350/1100/1200 for sensing the amount of light falling thereon. Additionally, the photo-sensitive element (e.g., a photo-electric circuit) would be placed into electrical communication with the CPU 900, so that software could utilize information provided thereby to alter the illuminative state of lights 970 as a function of the amount of light falling on the sensor, e.g., by turning the light sources "on" during low-light periods and "off" when the level of ambient light is higher, and/or by changing the color or intensity of the lights 970 during low light periods, etc. Note that the term "photo-sensitive circuit" should be interpreted broadly enough to include any photo-reactive device including, without limitation, a conventional photo-electric device, photovoltaic circuit, a photodiode, a phototransistor, a photo resistor, a CCD camera and a digital camera.

Figure 13:
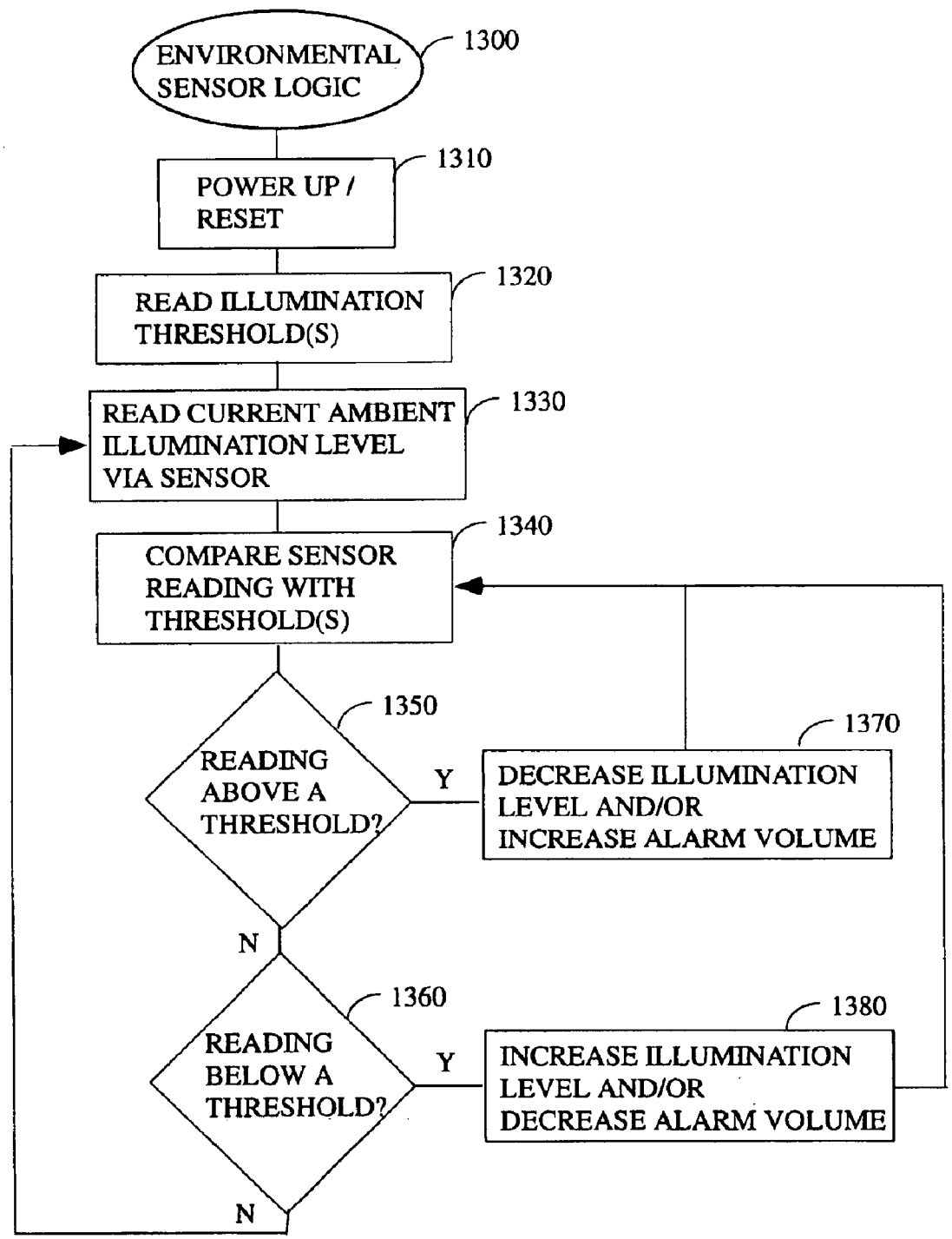
FIG. 13 illustrates another preferred embodiment of the instant invention, wherein the light source illuminative state and alarm volume are modified in response to changes in an environmental variable.

Note that FIG. 13 provides a specific example of how software to implement the above-described embodiment might operate in the case where the environmental sensor 990 is a photo-reactive circuit. That being said, those of ordinary skill in the art will recognize that any other sensor which can be used to monitor the environmental conditions in the vicinity of the patient, and which can communicate information about that environment to a microprocessor within an electronic patient monitor, would work as well. Examples of the sort of environmental quantities that it might prove to be useful to monitor include light, temperature, humidity, sound, motion, etc.

According to the preferred operating logic 1300 that is followed when an electronic patient monitor is used in conjunction with an environmental sensor 990, upon power up 1310 illumination thresholds will be read 1320, preferably from some sort of non-volatile internal storage. Of course, it is certainly possible that the threshold(s) could be read from the user each time the unit is powered up. However, that would be an inconvenience which the instant inventors would choose not to impose on the user. In a typical configuration there would be one or more numerical thresholds that specify the illumination settings at which the properties of the electronic patient monitor would be changed. That is, at a minimum one such threshold would be desired such that illumination levels above and below that threshold would be modified as is described below. However, those of ordinary skill in the art will recognize that multiple thresholds might be used with different lighting activity taking place within each threshold-interval or, alternatively, a function might be created that smoothly varies the properties of the light sources (or speaker volume) as the illumination level in the room changes. All of such is well within the ability of one of ordinary skill in the art to create. Thus, for purposes of the instant disclosure, the term "threshold" should be construed in its broadest sense to include discrete qualitative or quantitative threshold values, as well as functional expressions that relate the value obtained from the environmental sensor to the output level of some device.

Once the threshold definitions have been read, the preferred embodiment then enters an event loop which contains as a major components: reading the current ambient illumination level in the room via the photo-sensitive device 1330; comparing the sensor reading with the predetermined threshold levels 1340; and then testing to see whether a threshold has been crossed since the last reading (steps 1350 and 1360). In the preferred embodiment, if the current room lighting level has creased above a threshold boundary, the microprocessor will then decrease the illumination level of the light sources (step 1370). Note that this decrease may be incremental (i.e., to a lower brightness level), or it may take the form of powering off the light completely (i.e., deactivating it). In a case where the overall level of illumination in the room is decreasing, the program steps 1360 and 1380 will operate to increase (either incrementally or fully) the amount of light emitted from the patient monitor's light sources. Note that, for purposes of clarity, FIG. 13 illustrates only the logic associated with reading the attached environmental sensor. In normal operations there would be other activities within the main event loop including, without limitation, logic branches that check and respond to changes in the state of the patient monitor.

Additionally, it is contemplated that this same or a similar program logic can also be used to vary the volume of the alarm. In a preferred arrangement, the volume of the alarm will be decreased (step 1380) during the night (i.e., when the level of illumination is low) and increased again during day light hours (step 1370). Note that this same program logic can also accommodate changes in lighting, alarm volume, etc., which are made as a function of a predetermined time schedule, in which case the "thresholds" will correspond to the times of day at which the unit is to modify its behavior.

According to another preferred arrangement, there is provided an electronic patient monitor substantially as described above but wherein the intensity and/or color of the light sources 400/1110/1220 is automatically changed according to the time of day and/or the amount of ambient light falling thereon. In more particular, in the instant embodiment the configuration of FIG. 9 is preferably augmented by the addition of a clock chip 995 or similar timing circuit which in electronic communication with the CPU 900 and can be accessed and read thereby. Of course, it is not essential that a dedicated timing circuit external to the microprocessor be utilized, as the microprocessor could certainly contain such a circuit internally and/or use software methods well known to those of ordinary skill in the art (e.g., timing loops) to track the passage of time. Given the time of day, the instant embodiment would alter the illuminative state of light source 970 as a function of the time of day, e.g., by turning the lights "on" during the evening hours and "off" during daylight hours, or by changing the color or intensity of the lights 970 during the evening, etc. Note that, for purposes of the instant disclosure, that a clock circuit should be considered to be an "environmental sensor" in the sense that it measures a quantity different from that measured by the patient sensor 980.

Additionally, it should be noted that the instant inventors optionally contemplate that in those instances above wherein the lights sources are automatically activated/deactivated in response to environmental parameters, the alarm volume could also be modified in conjunction with the changing of the light source status. As an example, the alarm volume would optionally also be set to its lower/night volume when the CPU 900 detects that the level of ambient lighting is low and returned to its higher/day volume again when the unit senses a return of "day" levels of illumination.

As a further example, and in addition to the two embodiments mentioned previously, the instant inventors further contemplate that the illuminative state of the lights source might be modified in response to changes in ambient noise level (e.g., turning "on" in the presence of a loud noise which might correspond to a fall by a patient, or turning "on" if the ambient noise level is low, which might correspond to evening). In such a case, the environmental sensor 990 would be some sort of microphone or other sound-detecting circuitry. As another example, if the instant monitor is unplugged from the nurse call system, the light sources 970 might be activated to signal that fact to the caregiver, which light activation might be accompanied by activation of the patient monitor siren/internal alarm.

Conclusions

Although the preferred embodiment of the instant invention is designed to be used with an electronic patient monitor containing a microprocessor, that is not an essential element of the instant invention and it is certainly possible and within the ability of one of ordinary skill in the art to construct a simple analog patient monitor that is responsive to the patient detection circuit, and that can automatically switch and/or indicate night volume, but which does not contain a microprocessor. Thus, when the term "electronic patient monitor" is used herein, that term should be interpreted in its broadest sense to include both patient monitors that have—and those that do not have—controlling microprocessors, except where a microprocessor is specifically called for When the term microprocessor is used herein, it should be understood in its broadest sense to include any programmable device that is capable of recognizing signals from a patient sensor, setting internal parameter values based on external information, and responding to patient activity in accordance with the parameter values so set. These sorts of modest requirements may be satisfied by any number of programmable logic devices ("PLD") including, without limitation, gate arrays, FPGA's (i.e., field programmable gate arrays), CPLD's, EPLD's, SPLD's, PAL's, FPLA's, FPLS, GAL, PLA, FPAA, PSoC, SoC, CSoC, etc., as those acronyms and their associated devices are known and used in the art. Additionally, many devices contain microprocessors integral thereto, e.g., micro controllers, and the instant disclosure is intended to encompass those sorts of devices as well.

In the preferred arrangement, the exterior case of the electronic patient monitor will be generally rectangular in cross section (i.e., the case will usually take the form of a hollow "box"). That being said, the shape of the casing of the monitor is not crucial to the operation of the instant invention except in so far as the positioning of the lights is concerned in connection with the lighted splash guard. That is, whatever the shape of the monitor case it must be configured such that a light source can be placed on one "side" of the housing and a control panel on another, and that light can be transmitted from the light source to the control panel via internal transmission by the splash guard. With a traditional rectangular case, it should be clear what is meant by a light that is positioned on one side of the case and a control panel on another. With other shapes, however, the inventors intend that the control panel and light will be deemed to be on different "sides" of the monitor if the light source is positioned in such a way that it does not directly illuminate the control panel.

Further, when the term "light conducting material" is used herein in connection with the splash guard material, that term should be understood to include polycarbonate as well as any other transparent/translucent material that can conduct at least some light from a remote light source so that it falls upon the control panel of the electronic monitor, thereby indirectly illuminating it. No particular amount of transparency is required, however it should be clear that unless the material is at least somewhat transparent, insufficient light will be transmitted up to the control panel where it is needed.

Still further, it should be noted and remembered that the preferred electronic monitor includes programming instructions stored therein for execution by the microprocessor, which programming instructions define the monitor's response to the patient and environmental sensors. Although ROM is the preferred apparatus for storing such instructions, static or dynamic RAM, flash RAM, EPROM, PROM, EEPROM, or any similar volatile or nonvolatile computer memory could be used. Further, it is not absolutely essential that the software be permanently resident within the monitor, although that is certainly preferred. It is possible that the operating software could be stored, by way of example, on a floppy disk, a magnetic disk, a magnetic tape, a magneto-optical disk, an optical disk, a CD-ROM, flash RAM card, a ROM card, a DVD disk, or loaded into the monitor over a network as needed. Thus, "program memory" as that term is used herein should be interpreted in its broadest sense to include the variations listed above, as well as other variations that are well known to those of ordinary skill in the art.

Additionally, when the term "control panel" is used herein, that term should be understood in its broadest sense to mean one or more switches or other user-manipulable devices (e.g., wheels, knobs, etc.) by which the various operating characteristics of the patient monitor are modified. Thus, it is certainly possible that a patient monitor might have more then one "control panel" in this sense if, for example, a volume wheel were provided on the side of the unit and a reset button on the top.

In addition, in the claims that follow the phrase "changing the state" or "changing the illuminative state" of a light source is to be construed in its broadest sense to include turning the light source from "on" to "off", as well as changing its color, flashing the light source, blinking the light source, alternatively blinking/flashing multiple lights sources, changing the intensity (brightness) of the light source when the term "activate" is used herein in connection with the light sources 400, that term should be understood to apply to situations beyond simple "turning on" of the light. More generally, the term "activate" should also be construed to cover the case where the color of a multi-color LED is changed and/or any other change in state of the light source 400. Similarly, the term "deactivate" as used herein means to "turn off" the light as well as to change the color of a multi-color LED to another color, or return the light source 400 to its original illuminative state. Additionally, the term "activate" should be understood to mean "flash" if the light source 400 is currently powered-on, and deactivate should be understood to mean "stop flashing" and return to its previous steady illumination.

Finally, it should be noted that the term "nurse call" as that term has been used herein should be interpreted to mean, not only traditional wire-based nurse call units, but more also any system for notifying a remote caregiver of the state of a patient, whether that system is wire based or wireless. Additionally, it should be clear to those of ordinary skill in the art that it may or may not be a "nurse" that monitors a patient remotely and, as such, nurse should be broadly interpreted to include any sort of caregiver, including, for example, untrained family members and friends that might be signaled by such a system.

Thus, it is apparent that there has been provided, in accordance with the invention, a patient sensor and method of operation of the sensor that fully satisfies the objects, aims and advantages set forth above. While the invention has been described in conjunction with specific embodiments thereof, it is evident that many alternatives, modifications and variations will be apparent to those skilled in the art and in light of the foregoing description. Accordingly, it is intended to embrace all such alternatives, modifications and variations as fall within the spirit of the appended claims.

What is claimed is:

1. A device for monitoring a changing status of a patient, comprising:
   (a) an electronic patient monitor, said electronic patient monitor having an exterior case, said exterior case
      (i) having at least two sides,
      (ii) having a monitor control panel positioned on a first side of said exterior case, and,
      (iii) having at least one light source positioned on a second side of said exterior case, said at least one light source being oriented so that light emitted therefrom does not fall directly on said control panel when said at least one light source is activated; and,
   (b) a splash guard positionable to enclose at least a portion of said monitor control panel and proximate to said at least one light source, said splash guard being made of a light conducting material and positionable to receive and internally transmit at least a portion of the light emitted from said at least one light source so as to indirectly illuminate said control panel.

2. The device for monitoring a changing status of a patient according to claim 1, further comprising:
   (c) a patient sensor positionable to be in electronic communication with said electronic patient monitor and positionable to be proximate to the patient, said patient sensor for detecting the changing status of the patient.

3. The device for monitoring a changing status of a patient according to claim 2 wherein said patient sensor is selected from a group consisting of a pressure sensitive mat, a wetness sensor, and an activity sensor.

4. The device for monitoring a changing status of a patient according to claim 2, wherein said electronic patient monitor, comprises:
   (a1) a microprocessor, said microprocessor being in electronic communication with said at least one light source, with said patient sensor, and with said control panel,
      (i) said microprocessor being responsive to a program resident therein,
      (ii) said microprocessor at least for receiving user input from said control panel according to said program,
      (iii) said microprocessor at least for controlling said at least one light source according to said program, and,
      (iv) said microprocessor at least for synthesizing at least one alarm sound according to said program,
   (a2) a speaker in electronic communication with said microprocessor, said speaker for emitting alarms synthesized by said microprocessor.

5. The device for monitoring a changing status of a patient according to claim 4, wherein said program resident within said microprocessor comprises computer instructions to at least perform the steps of:
   (a) reading a value representative of a day alarm volume and a value representative of a night alarm volume;
   (b) determining a current alarm volume by selecting between said day alarm volume and said night alarm volume according to the desires of a user;
   (c) determining an initial status of the patient using said patient sensor;
   (d) determining a current status of the patient using said patient sensor;
   (e) repeating step (d) at least until said current status of the patient is different from said initial status of the patient;
   (f) sounding an alarm through said speaker at a volume level approximately equal to said current alarm volume if said current status of the patient is different from said initial status of the patient;
   (g) automatically activating at least one of said at least one light source while said alarm is sounded; and,
   (h) deactivating said at least one of said at least one light source when said alarm is ended.

6. The device for monitoring a changing status of a patient according to claim 4, wherein said program resident within said microprocessor at least comprises computer instructions for performing at least the steps of:
   (a) reading a value representative of a day alarm volume level and a value representative of a night alarm volume level, said day alarm volume level being greater than said night alarm level,
   (b) determining a current speaker volume by selecting between said day speaker volume and said night speaker volume according to the desires of a user;
   (c) automatically activating at least one of said at least one light source if said current speaker volume is less than or equal to said night speaker volume; and,
   (d) automatically deactivating at least one of said at least one light source if said current speaker volume is greater than or equal to said day speaker volume.

7. The device for monitoring a changing status of a patient according to claim 1, wherein at least one of said at least one light source penetrates at least partially into said light conducting material of said splash guard.

8. A device for monitoring a changing status of a patient according to claim 2, wherein is provided a predetermined night volume level, further comprising:
   (c) a speaker, said speaker being at least for broadcasting an alarm depending on the changing status of the patient;
   (d) a volume control,
      (d1) said volume control for adjusting a volume of said alarm, and
      (d2) said volume control having a plurality of different volume levels which are selectable by a user; and,
   (e) a light activation circuit in electronic communication with said volume control and said at least on light source, said light activation circuit
      (i) automatically activating at least one of said at least one light source when the user said volume control to a volume level less than or equal to said predetermined night volume level, and (ii) automatically deactivating said at least one of said at least one light source when the user sets said volume control to a volume level above said predetermined night volume level.

9. A device far monitoring a changing status of a patient according to claim 8, wherein said volume control is a digital volume control.

10. A device for monitoring a changing status of a patient according to claim 2, wherein is provided a predetermined night volume level and a predetermined day volume level, said day volume level being greater than said night volume level, further comprising:
   (c) a speaker, said speaker being at least for broadcasting an alarm depending on the changing status of the patient;
   (d) a volume control,
      (d1) said volume control for adjusting a volume of said alarm, and
      (d2) said volume control having a plurality of different volume levels which are selectable by a user; and,
   (e) a light activation circuit in electronic communication with said volume control and said at least one light source, said light activation circuit
      (i) automatically activating at least one of said at least one light source when the user sets said volume control to a volume level less than or equal to said predetermined night volume level, and,
      (ii) automatically deactivating said at least one of said at least one light source when the user sets said volume control to a volume level above said predetermined day volume level.

11. The device for monitoring a changing status of a patient according to claim 8, wherein said light activation circuit, comprises:
   (e1) a microprocessor, said microprocessor being in electronic communication with said at least one light source with said patient sensor, and with said volume control, wherein said microprocessor is responsive to a program resident therein, wherein said program comprises a plurality of instructions, said plurality of instructions including at least instructions for
      (i) receiving user input from said volume control,
      (ii) automatically activating at least one of said at least one light source when the user sets said volume control to a volume level less than or equal to said predetermined night volume level,
      (iii) automatically deactivating said at least one of said at least one light source when the user sets said volume control to a volume level above said predetermined night volume level,
      (iv) monitoring the changing state of the patient using said patient sensor, and,
      (v) initiating an alarm through said speaker depending on the state of the patient.

12. The device for monitoring a changing status of a patient according to claim 1, wherein said light conducting material is polycarbonate.

13. The device for monitoring a changing status of a patient according to claim 1,
   wherein there are a plurality of light sources positioned on said second side of said exterior case, and
   wherein said plurality of light sources are oriented so that light emitted from said plurality of light sources does not fall directly on said control panel when said light sources are activated.

14. An electronic patient monitor according to claim 1, wherein said program at least contains commands comprising:
   (i) sounding an alarm in response to a change in the status of the patient, and,
   (ii) automatically varying an alarm volume in response to a measurement of light level obtained from said photoelectric sensor, wherein said alarm volume is increased when said level of light proximate to said electronic patient monitor increases, and wherein said alarm volume is decreased when said level of light proximate to said electronic patient monitor decreases.

15. A method of alerting a caregiver when a status of a patient has changed, wherein is provided a patient sensor positionable to be proximate to said patient, and a patient monitor in electronic communication with said patient sensor, wherein
   said patient monitor is at least for monitoring the status of a patient and for sounding an alarm in response to the status of the patient,
   said patient monitor has an enclosing case, said enclosing case having a splash guard attached thereto, wherein said splash guard is comprised of optically conductive material, and,
   said patient monitor has at least one light source positioned on said enclosing case, said at least one light sources being in direct optical communication with said splash guard,
   comprising the steps of:
   (a) using said patient sensor to determine an initial status of the patient;
   (b) setting said at least one light source to an initial illuminative state;
   (c) determining a current status of the patient;
   (d) repeating step (c) until said current status of the patient is different from said initial status of the patient;
   (e) sounding said alarm if said current status of the patient is different from said initial status of the patient;
   (f) contemporaneously with said step (e), changing said illuminative state of said light source to an illuminative state different from said initial illuminative state, thereby providing at least via said splash guard a visual indication that said alarm is being sounded.

16. The method according claim 15, wherein step (b) comprises the steps of:
   (b1) selecting one or more of said at least one light source,
   (b2) deactivating said selected one or more light source, and wherein step (f) comprises the step of:
   (f1) contemporaneously with said step (e) activating said selected one or more light sources, thereby providing at least via said splash guard a visual indication that said alarm is being sounded.

17. The method according claim 15, wherein step (b) comprises the step of powering on one or more of said at least one light source, and wherein step (f) comprises the step of contemporaneously with said step (e), flashing said one or more powered-on light sources, thereby providing at least via said splash guard a visual indication that said alarm is being sounded.

18. The method according claim 15,
   wherein at least one of said at least one light source is a multi-color light source,
   wherein step (b) comprises the step of activating one or more of said multi-color light sources in a first color, and
   wherein step (f) comprises the step of, contemporaneously with said step (e), activating said one or more multi-color light sources in a second color different from said first color, thereby providing at least via said splash guard a visual indication that said alarm is being sounded.

19. A method of indicating a current alarm volume level of an electronic patient monitor to a user,
wherein said patient monitor is at least for monitoring a status of a patient and for sounding an audible alarm in response to a change in the status of the patient,
said alarm having at least two user-specifiable alarm volume levels,
wherein said patient monitor has an enclosing case, and,
wherein said patient monitor has at least one light source positioned on said enclosing case,
each of said at least one light source having at least two different illuminative states,
each of said at least two user-specifiable alarm volume levels corresponding to at least one of said at least two illuminative states of said at least one light source,
comprising the steps of:
(a) reading a value representative of an initial alarm volume level;
(b) choosing a current alarm volume level from among said at least two alarm volume levels based on said value representative of said initial alarm volume level;
(c) determining an initial illuminative state corresponding to said initial alarm volume level;
(d) automatically setting said current illuminative state of said at least one light source to match said initial illuminative state;
(e) reading from the user a value representative of a modified alarm volume level;
(f) changing said current alarm volume level of said electronic patient monitor to at least approximately equal said modified alarm volume level;
(e) determining a current illuminative state of said at least one light source corresponding to said value representative of said modified alarm; and,
(f) automatically setting said at least one light source to match said current illuminative state, thereby indicating said current alarm volume level of an electronic patient monitor to a user.

20. The method according claim 19, wherein at least one of said at least two illuminative states corresponds to "power on" and another of said at least two illuminative states corresponds to "power off".

21. The method according claim 19, wherein at least one of said at least one light source is a multi-color light source, and wherein one of said at least two illuminative states corresponds to activation of a first color and another of said at least two illuminative states corresponds to activation of a second color.

22. A method of modifying the operating characteristics of an electronic patient monitor in response to changes in the environment of the patient, wherein is provided a patient sensor positionable to be proximate to said patient, and a patient monitor in electronic communication with said patient sensor,
wherein said patient monitor is at least for monitoring a status of a patient and for sounding an alarm in response to a change in the status of the patient,
wherein said patient monitor has an enclosing case,
wherein said patient monitor has a microprocessor therein,
wherein said patient monitor has at least one light source positioned on said enclosing case,
said at least one light source being capable of displaying a plurality of illuminative states, and
said at least one light source being in electronic communication with said microprocessor and being at least partially controlled thereby, and,
wherein said patient monitor has at least one environmental sensor therein, said at least one environmental sensor being in electronic communication with said microprocessor and readable by said microprocessor to yield a value of an environmental variable,
comprising the steps of:
(a) reading said environmental sensor to determine an initial state of a patient environment;
(b) setting said at least one light source to a first illuminative state corresponding to said initial state of the patient environment;
(c) reading said environmental sensor, thereby determining a current state of the patient environment;
(d) performing step (c) until said current state of the patient environment is different from said initial state of the patient environment;
(e) if said current state of the patient environment is different from said initial state of the patient environment,
(1) determining a second illuminative state corresponding to said current state of the patient environment, and,
(2) setting said at least one light source to said second illuminative state corresponding to said current state of the patient environment, thereby modifying the operating characteristics of said electronic patient monitor in response to a change in the environment of the patient.

23. The method according claim 22, wherein said environmental sensor is a photo-electric sensor and step (e)(2) comprises the step of:
(e2) powering up said at least one light sources if said current state of the patient environment is a reduced level of illumination compared with said initial state of the patient environment, and, powering down said at least one light sources if said current state of the patient environment is an increased level of illumination compared with said initial state of the patient environment.

24. The method according claim 23, wherein said electronic patient monitor is for sounding an audible alarm, and wherein said electronic patient monitor has at least two different alarm volumes, further comprising the step of:
(f) if said current state of the patient environment is different from said initial state of the patient environment,
(1) decreasing said alarm volume if said current state of the patient environment is a reduced level of illumination compared with said initial state of the patient environment, and,
increasing said alarm volume if said current state of the patient environment is an increased level of illumination compared with said initial state of the patient environment.

25. An electronic patient monitor for monitoring a changing status of a patient, comprising:
(a) a patient sensor positionable to be proximate to the patient, said patient sensor for measuring the changing status of the patient when so positioned;
(b) an environmental sensor, said environmental sensor for determining a value representative of an environmental condition proximate to said electronic patient monitor;

(c) at least one light source, said at least one light source having at least two different illuminative states;

(d) a microprocessor in electronic communication at least with said environmental sensor, with said patient sensor, and with said at least one light source, said microprocessor being responsive to a computer program resident therein, said computer program at least containing commands for (i) sounding an alarm in response to a change in the status of the patient, and, (ii) automatically changing between said at least two illuminative states of said at least one light sources depending on said value representative of said environmental condition; and, (e) an audio speaker in electronic communication with said microprocessor, said audio speaker at least for emitting alarm sounds at a plurality of different volume levels under control of said microprocessor.

26. The electronic patient monitor according to claim 25, wherein step (i) comprises the step of sounding an alarm through said audio speaker in response to a change in the status of the patient.

27. The electronic patient monitor according to claim 25, wherein the environmental sensor is selected from the group consisting of a time circuit, a photo-sensitive circuit, a microphone, a temperature sensor, and a humidity sensor.

28. The electronic patient monitor according to claim 25, wherein step (i) comprises the step of sounding an alarm through said audio speaker in response to a change in the status of the patient.

29. The electronic patient monitor according to claim 25, wherein said environmental sensor is a photo-electric sensor integral to said electronic patient monitor, said photo-electric sensor for determining at least approximately a value representative of a level of light proximate to said electronic patient monitor.

30. An electronic patient monitor according to claim 29, wherein at least one of said illuminative states of said at least one light source corresponds to "activation", and wherein another of said at least one illuminative states of said at least one light source corresponds to "deactivation", and wherein said computer program at least contains commands for:

(i) sounding an alarm in response to a change in the status of the patient, and, (ii) automatically changing between said at least two illuminative states of said at least one light sources according to said value representative of the level of light proximate to said electronic patient monitor, wherein at least one of said at least one light sources is activated when said level of light decreases, and wherein at least one of said at least one light sources is deactivated when said level of light increases.

31. An electronic patient monitor according to claim 30, wherein step (i) comprises:

(i1) determining an alarm volume based on said value representative of said level of light proximate to said electronic patient monitor, (i2) sounding an alarm through said audio speaker at a volume at least approximately equal to said determined alarm volume.

32. An electronic patient monitor according to claim 31, wherein the step of determining an alarm volume based on said level of light proximate to said electronic patient monitor comprises the steps of determining to increase said alarm volume if said level of light proximate to said electronic patient monitor increases, and determining to decrease said alarm volume if said level of light proximate to said electronic patient monitor decreases.

33. An electronic patient monitor for monitoring a changing status of a patient, wherein is provided a patient sensor positionable to be proximate to the patient, said patient sensor measuring the changing status of the patient when so positioned, comprising:

(a) a photo-electric sensor integral to said electronic patient monitor, said photo-electric sensor for determining at least approximately a level of light proximate to said electronic patient monitor;

(b) a microprocessor at least in electronic communication with said photo-electric sensor and with said patient sensor, said microprocessor being responsive to a program resident therein, said program at least containing commands for (i) sounding an alarm in response to a change in the status of the patient, and, (ii) automatically varying an alarm volume in response to a measurement of light obtained from said photo-electric sensor; and, (c) an audio speaker in electronic communication with said microprocessor, said audio speaker at least for emitting alarm sounds at a plurality of different volume levels under control of said microprocessor.

\* \* \* \* \*

UNITED STATES PATENT AND TRADEMARK OFFICE
CERTIFICATE OF CORRECTION

PATENT NO. : 6,864,795 B2
DATED : March 8, 2005
INVENTOR(S) : Smith et al.

It is certified that error appears in the above-identified patent and that said Letters Patent is hereby corrected as shown below:

<u>Column 19,</u>
Line 5, after the word "device," the word "far" is replaced with the word -- for --

Signed and Sealed this

Seventeenth Day of May, 2005

JON W. DUDAS
*Director of the United States Patent and Trademark Office*